(12) United States Patent
Dyson et al.

(10) Patent No.: US 9,018,199 B2
(45) Date of Patent: Apr. 28, 2015

(54) TRANSITION METAL COMPLEXES FOR INHIBITING RESISTANCE IN THE TREATMENT OF CANCER AND METASTASIS

(75) Inventors: Paul Joseph Dyson, Ecublens (CH); Wee Han Ang, Ecublens (CH)

(73) Assignee: Ecole Polytechnique Federale de Lausanne (EPFL), Lausanne (CH)

( * ) Notice: Subject to any disclaimer, the term of this patent is extended or adjusted under 35 U.S.C. 154(b) by 1625 days.

(21) Appl. No.: 12/227,210

(22) PCT Filed: May 9, 2007

(86) PCT No.: PCT/CH2007/000234
§ 371 (c)(1),
(2), (4) Date: Apr. 2, 2009

(87) PCT Pub. No.: WO2007/128158
PCT Pub. Date: Nov. 15, 2007

(65) Prior Publication Data
US 2009/0312301 A1    Dec. 17, 2009

Related U.S. Application Data

(60) Provisional application No. 60/799,433, filed on May 9, 2006.

(51) Int. Cl.
C07F 15/00 (2006.01)
A61K 31/28 (2006.01)
A61K 31/555 (2006.01)
A61P 35/00 (2006.01)

(52) U.S. Cl.
CPC ........... *C07F 15/0046* (2013.01); *C07F 15/002* (2013.01); *C07F 15/0033* (2013.01); *C07F 15/0073* (2013.01)

(58) Field of Classification Search
None
See application file for complete search history.

(56) References Cited

U.S. PATENT DOCUMENTS

| | | | |
|---|---|---|---|
| 4,980,473 | A | 12/1990 | Barton |
| 6,207,091 | B1 | 3/2001 | Kanamoto et al. |
| 2005/0239765 | A1 | 10/2005 | Morris et al. |
| 2006/0058270 | A1 | 3/2006 | Sadler et al. |

FOREIGN PATENT DOCUMENTS

| | | |
|---|---|---|
| WO | WO 01/30790 A | 5/2001 |
| WO | WO 02/102572 A1 | 12/2002 |
| WO | WO 2006/018649 | 2/2006 |

OTHER PUBLICATIONS

Champlin et al. "Effect of outer membrane permeabilisation on intrinsic resistance to low triclosan levels in *Pseudomonas aeruginosa*", International Journal of Antimicrobial Agents, 2005, 26, 159-164.*

(Continued)

*Primary Examiner* — Kortney L Klinkel
(74) *Attorney, Agent, or Firm* — Krieg DeVault LLP

(57) ABSTRACT

The present invention relates to organometallic compounds useful in the treatment of metastasis. The organometallic compounds comprise a ligand that is covalently bound to a bioactive compound, which is an inhibitor of a resistance pathway or a derivative thereof. Preferably, the organometallic compounds are half-sandwich ("piano-stool") compounds. The compounds of the present invention offer a high variability with respect to the bioactive compound and to the nature of the ligand bound to a central transition metal.

19 Claims, 3 Drawing Sheets

(56) References Cited

OTHER PUBLICATIONS

Wang et al. "Competition between glutathione and guanine for a Ruthenium(II) arene anticancer complex: Detection of a sulfenato intermediate", J. Am. Chem. Soc. published on web Nov. 23, 2005, 127, 17734-17743.*

Missling et al. "Organometallic complexes of Ruthenium(II), Rhodium(III), Iridium(III), and Gold(I) with cinchona alkaloids" Chem. Ber. 1996, 129, 331-335.*

Allardyce et al. ("Ruthenium in Medicine: Current Clinical Uses and Future Prospects" Platinum Metals Rev. 2001, 45(2), 62-69).*

Ang et al.; Rational Design of Platinum(IV) Compounds . . . ; JACS Communications; 1382 J. Am. Chem. Soc. 205, 127, 1382-1383; XP-002422722.

Serli et al.; Is the Aromatic Fragment of Piano-Stool Ruthenium . . . ; Eur. J. Inorg. Chem 2005, 3423-3434; XP-002422723.

* cited by examiner

TRANSITION METAL COMPLEXES FOR INHIBITING RESISTANCE IN THE TREATMENT OF CANCER AND METASTASIS

This application claims the benefits under 35 U.S.C. 119 (a)-(d) or (b), or 365(b) of International Application No. PCT/CH2007/000234 filed 9 May 2007, and U.S. Provisional Patent Application No. 60/799,433 filed 9 May 2006.

This invention relates to organometallic compounds of the metals Ru, Os, Rh, and Ir, to their use in medicine, particularly for the treatment and/or prevention of cancer, and more particularly in the treatment of metastasis. This new class of compounds contains, covalently bound to any of the ligands of the metal, or directly to the metal, a bioactive organic compound which is an inhibitor of resistance pathway.

BACKGROUND AND OBJECTIVES OF THE INVENTION

Resistance against bioactive principles that directly target the origin of a disease are widespread, and one or more of a number of known resistance pathways are at their origin. For example, the Glutathione-S-Transferase (GST) is a superfamily class of isozymes that constitute the main cellular defense against xenobiotics, including bioactive principle designed for the treatment of a disease. They catalyse the conjugation of endogenous glutathione (GSH) with the electrophilic groups of substrates, the first step in the mercapturic acid pathway that leads to elimination of toxic compounds. The overexpression of several subclasses of GST, namely GST-$\pi$ r and GST-$\alpha$, has been linked to the multidrug resistance phenomenon of certain anticancer drugs, such as cisplatin and adriamycin. More recently, GSTP1-1 (GST-$\pi$ subclass) was found to mediate the c-Jun N-Terminal Kinase (JNK) signal transduction pathway, an important control of cell survival. It was found to have a significant affinity for the C terminus of JNK and therefore could potentially interfere with and suppress downstream induction of cellular apoptosis. Clearly, GST is a potential target for chemotherapeutic drug design, in order to inhibit resistance against anti-cancer drugs.

Ruthenium-based compounds have shown some potential as anticancer drugs. For example, U.S. Pat. No. 4,980,473 discloses 1,10-phenanthroline complexes of ruthenium(II) and cobalt(II) which are said to be useful for the treatment of tumour cells in a subject.

Some other ruthenium(II) and ruthenium(III) complexes which have been shown to exhibit antitumour activity are mentioned in Guo et al, Inorganica Chimica Acta, 273 (1998), 1-7, specifically trans-[RuCl$_2$(DMSO)$_4$], trans-[RuCl$_4$(imidazole)$_2$] and trans-[RuCl$_4$(indazole)$_2$]. Clarke et al have reviewed the anticancer, and in particular the antimetastatic, activity of ruthenium complexes: Chem. Rev., 1999, 99, 251-253. Also, Sava has reviewed the antimetastatic activity in "Metal Compounds in Cancer Therapy" Ed by S P Fricker, Chapman and Hall, London 1994, p. 65-91.

Dale et al, Anti-Cancer Drug Design, (1992), 7, 3-14, describes a metronidazole complex of ruthenium(II) ie, [(C$_6$H$_6$)RuCl$_2$(metronidazole)] and its effect on DNA and on E. coli growth rates. Metronidazole sensitises hypoxic tumour cells to radiation and appears to be an essential element of the complexes of Dale et al. There is no indication that the complexes would be at all effective in the absence of the metronidazole ligand.

Kramer et al, Chem Eur J., 1996, 2, No. 12, p. 1518-1526 discloses half sandwich complexes of ruthenium with amino esters. Bennett et al, Canadian Journal of Chemistry, (2001), 79, 655-669 discloses certain ruthenium(II) complexes with acetylacetonate ligands. Oro et al, J Chem Soc, Dalton Trans, (1990), 1463 describes ruthenium(II) complexes containing -p-cymene and acetylacetonate ligands. WO 01/130790 discloses ruthenium(II) compounds and their use as anticancer agents. The compounds have neutral N-donor ligands and the resulting ruthenium complex is generally positively charged.

WO 02/102572 also discloses ruthenium(II) compounds that have activity against cancer cell lines. Again, the complexes are generally positively charged. Complexes are disclosed containing a bidentate ligand which is a neutral diamine ligand.

Chen et al, J. Am. Chem. Soc., volume 124, no 12, 3064, (2002), describes the mechanism of binding of ruthenium complexes to guanine bases. The binding model requires NH bonds from a diamino ligand to be present in the complex for hydrogen bonding to the guanine base. Similarly, Morris et al, J. Med. Chem., volume 44, 3616-3621, (2001), describes the selectivity of ruthenium(II) complexes for binding to guanine bases.

Further references concerned with Ruthenium complexes for treatment of cancer are WO 06/018649, US 2006/0058270, US 2005/0239765.

Very few, if any, of the compounds and complexes of the prior art cited above have resulted in clinical phase studies, not to mention actual therapies. The reason for the poor performance of these principles are manifold and may be linked to toxicity problems or un-sufficient efficiency in treatment.

It is thus an objective of the present invention to explore new ways for treating cancer, for example based on work done in the area of complexes of transition metals.

It is a further aspect of the present invention to increase the activity and/or efficiency of therapies against diseases and in particular cancer. More particularly, it is an objective to reduce the resistance intrinsic to or developed against therapies, and in particular against resistance in cancer chemotherapies. By reducing resistance to bioactive principles against diseases an in particular cancer, it is hoped to increase the overall efficiency of the therapy. With increased efficiency, lower levels of the bioactive principle needs to be administered, which may further reduce side effects linked to the treatment.

Tumors of various kinds can be removed surgically, the most relevant problem of these cancers being the development of metastasis. It is thus an objective of the present invention to prevent and/or treat metastasis. In particular, it is an objective of the invention to assist the treatment for prevention and/or treatment of metastasis.

SUMMARY OF THE INVENTION

The present invention relates to complexes of transition metals comprising ligands in any form and of any nature, with the proviso that at least one of the ligands comprises at least one bioactive organic compound selected from inhibitors of resistance pathways and/or pharmaceutically acceptable derivatives thereof. Inhibitors may be directly attached to the transition metal as a ligand, or it may be covalently bound to a ligand of the transition metal.

Remarkably, the present inventors observed low toxicity and high inhibition of resistance pathways when administering the organometalic compounds of the present invention. Surprisingly, high proliferation inhibition of the organometallic compounds of the present invention on carcinoma cells was observed. Moreover, toxicity against healthy, normal cells remained very low.

Accordingly, in a first aspect, the present invention provides an organometalic compound of the general formula (I),

which may be charged or neutral, and which may be present in the form of a salt and/or an optically resolved enantiomer, in which, M is a transition metal selected from the group of Ru, Os, Rh, and Ir, $R_1$, $R_2$, $R_3$, $R_4$, $R_5$, $R_6$ are neutral or charged ligands of the transition metal, whereby two, three or more of the ligands $R_1$, $R_2$, $R_3$, $R_4$, $R_5$, $R_6$ may be present in the form of one or more single compounds, the single compound being a bi-, tri- or polydentate compound, and/or, an alkene, alkyne, cyclopentadienyl and/or an arene, the alkene, alkyne, cyclopentadienyl and/or an arene being optionally substituted and optionally comprising one or more heteroatoms;

in which at least one bioactive organic compound selected from inhibitors of resistance pathways, related compounds, and/or derivatives of any of the fore-mentioned, is present in the organometallic compound, whereby the bioactive organic compound is directly attached to the metal, thus constituting at least one of the ligands selected from $R_1$-$R_6$, and/or is covalently bound to any of the ligands selected from $R_1$-$R_6$.

In a second aspect, the present invention provides the organometallic compounds of the invention for use as a medicament.

In a third aspect, the present invention provides the organometallic compounds of the invention in the preparation of a medicament for the inhibition of resistance pathways and/or for treating cancer, and in particular metastasis.

In a fourth aspect, the present invention provides a method for treating and/or preventing metastasis, the method comprising the step of administering to an individual an effective amount of the organometallic compound according to the invention.

In a fifth aspect, the present invention provides a method for treating and/or preventing metastasis the method comprising the step of administering to an individual an effective amount of an anti-cancer drug and, in parallel, an effective amount the organometallic compound according to the invention.

In the figures.

DETAILED DESCRIPTION OF THE PREFERRED EMBODIMENTS OF THE INVENTION

Figure 1:
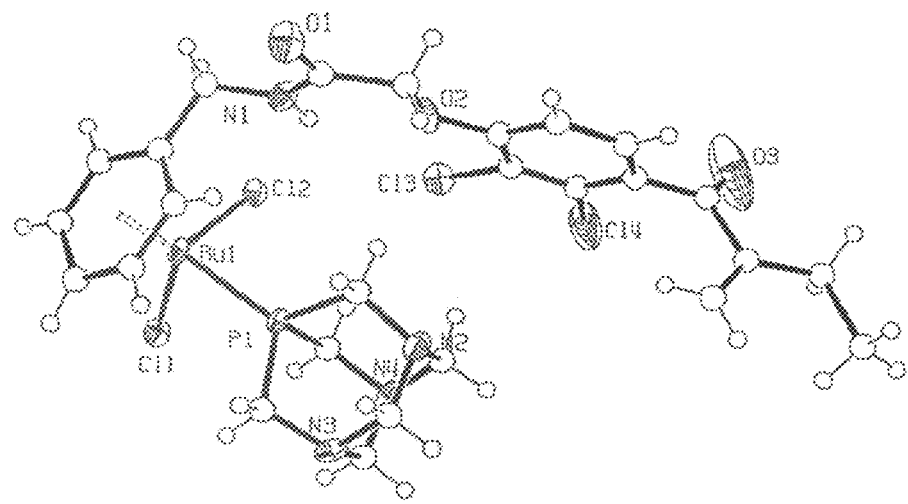
FIG. 1 shows a single crystal X-ray diffraction structure of compound (3), which is an example of an organometallic compound of the invention.
Figure 2:
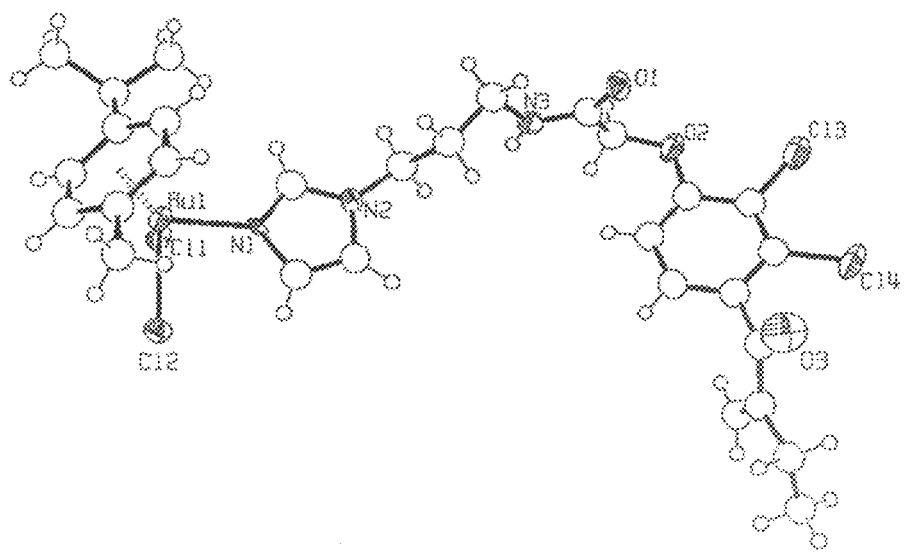
FIG. 2 shows a single crystal X-ray diffraction structure of compound (6), which is an example of an organometallic compound of the invention.
Figure 3:
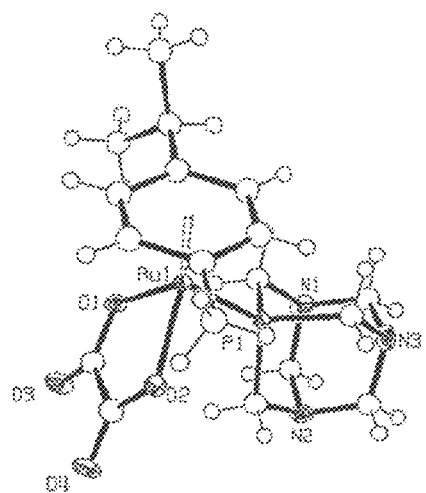
FIG. 3 shows a single crystal X-ray diffraction structure of compound (8), which is an organometallic compound having, amongst others, oxalate as a bivalent ligand.
Figure 4:
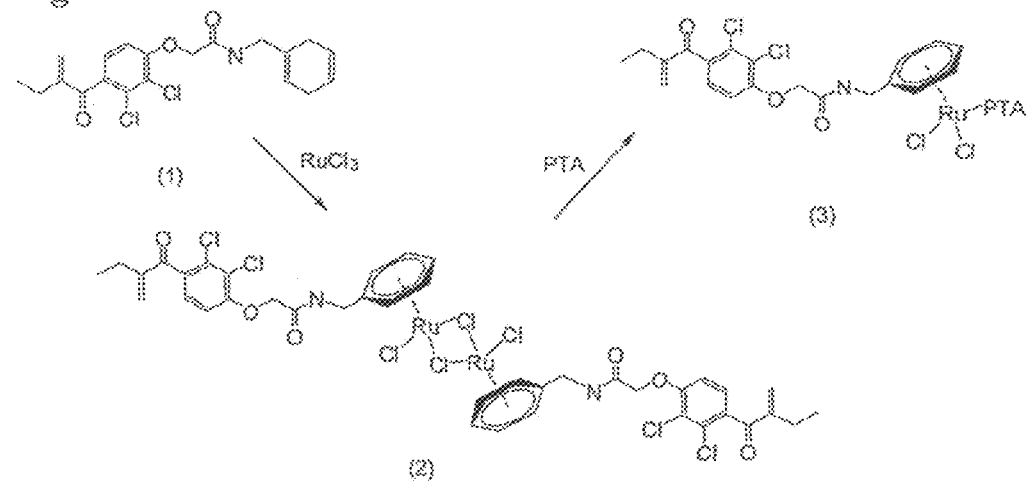
FIG. 4 illustrates the process for preparing (3), an example of an organometallic compound of the invention.
Figure 5:
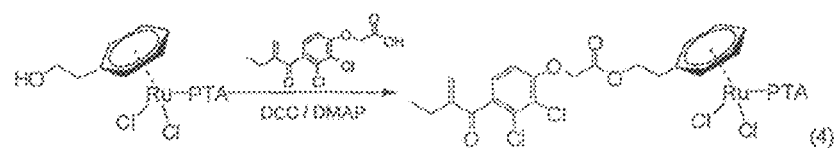
FIG. 5 illustrates the process for preparing (4), an example of an organometallic compound of the invention.
Figure 6:
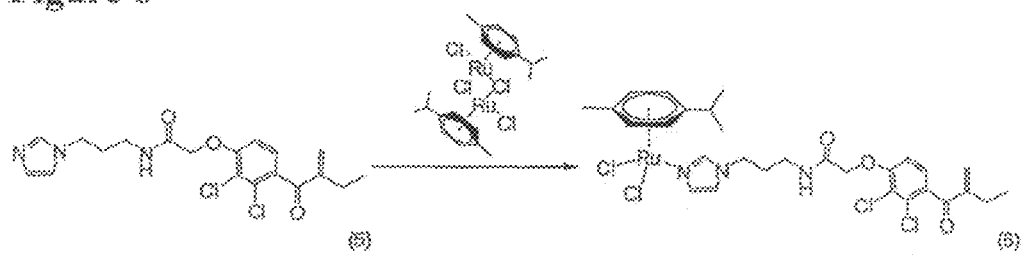
FIG. 6 illustrates the process for preparing (6), an example of an organometallic compound of the invention.

The present invention relates to organometallic compounds and their use as medicaments. The organometallic compound comprises a transition metal M, and, linked to the transition metal, a number of ligands. Ligands include donors of electron pairs and/or donors of π-orbitals from unsaturated bonds in organic molecules, for example.

The term "comprise" or "comprising", for the purpose of the present invention is intended to mean "including amongst other". It is not intended to mean, "consisting only of".

The transition metal M is selected from the group of Ru, Os, Rh, and Ir. Preferably, M is Ruthenium. The transition metal may be present in any oxidation state known with respect to the specific transition metal. For example, the oxidation state may be II or III. Preferably, M is Ruthenium (II).

$R_1$, $R_2$, $R_3$, $R_4$, $R_5$, $R_6$ are neutral or charged ligands attached to the transition metal. Suitable ligands include halogen ions, such as $F^-$, $Cl^-$, $Br^-$ and $I^-$, preferably chloride. One, two or more ligands selected from $R_1$-$R_6$ may be provided by halogens.

The term "selected from" a group indicated by "$R_1$-$R_6$", for example, or "any of $R^{N1}$-$R^{N3}$" as in the above paragraph or indicated below, respectively, refers to the fact that one or more selected from all the individuals of the group may be selected independently of each other. Accordingly, if one specimen of $R_1$-$R_6$ is to be selected, any one of $R_1$, $R_2$, $R_3$, $R_4$, $R_5$, $R_6$ can be selected.

One, two, three or more of the ligands $R_1$, $R_2$, $R_3$, $R_4$, $R_5$, $R_6$ may be selected from ligands providing electron pairs. For example, the ligands may be selected from N-, P-, O- or S-donor ligands. Preferably, at least one ligand of the organometallic compound of the invention is selected from N-, P-, O- or S-donor ligands. For example, at least one N-donor and/or at least one P-donor ligand is present.

Examples of N-donor ligands are nitrile ligands (N≡C—R); azo ligands (N=N—R); aromatic N-donor ligands; amine ligands ($NR^{N1}R^{N2}R^{N3}$); azide ($N_3^-$; cyanide (N≡C$^-$); isothiocyantate NCS$^-$).

In both nitrile and azo ligands, R may be selected from alkyl, alkenyl, alkynyl, and aryl, optionally substituted and optionally comprising one or more heteroatoms.

Aromatic N-donor ligands include optionally substituted pyridine, pyridazine, pyrimidine, purine and pyrazine, for example. Substituents may be selected from alkyl, alkenyl, alynyl, and aryl, optionally substituted and optionally comprising one or more heteroatoms.

$R^{N1}$, $R^{N2}$, and $R^{N3}$ may, independently of each other, be selected from H, alkyl, alkenyl, alkynyl, aryl, optionally substituted and optionally comprising one or more heteroatoms.

Preferably, two or all three of $R^{N1}$-$R^{N3}$ may be fused to form a cyclic N-donor compound. Furthermore, any of $R^{N1}$-$R^{N3}$ may be linked covalently to any other ligand of M, to provide bi-, tridenate or other polyvalent ligands. Preferably, $R^{N1}$, $R^{N1}$, and $R^{N3}$ are, independently of each other, selected from H and $C_{1-8}$ alkyls, optionally substituted.

According to a preferred embodiment, at least one of the ligands selected from $R_1$-$R_6$ is an N-donor ligand comprising the structure of formula (II) below,

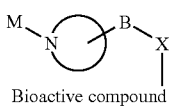

(II)

in which,

M is the transition metal;

the circle represents a mono- or polycyclic system, comprising at least one N-heteroatom, indicated as N, which provides an electron pair enabling attachment to M;

B is an optional linking group, which may be selected from alkyl, alkenyl, alkynyl and aryl, which is optionally substituted, which optionally comprises one or more heteroatoms and has 0-15, preferably 1-8 carbon atoms;

X is a functional group of B or the cyclic system, through which the bioactive compound is bound to B or to the cyclic system.

The cyclic system may further be substituted.

Preferably, in formula (II), the circle is a heterocyclic ring, for example a heterocyclic arene.

Preferably, it is a 5- or 6-membered heterocyclic ring, for example arene. Preferably, A is a $C_1$-$Cl_6$, more preferably a $C_2$-$C_4$ alkylene.

Preferably, X is selected from —O— and from —NH—. Accordingly, X preferably represents an ether, ester or peptide group, of which the carbonyl part, if applicable, may be part of the "bioactive compound" or of B.

According to a particularly preferred embodiment, any one of the ligands selected from $R_1$-$R_6$ is a N-donor ligand comprising the structure of formula (III) below, to which the bioactive compound is linked by means of an amide bond:

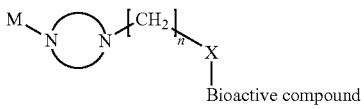

(III)

in which, the dashed line represents bonding, as a monodentate ligand, to the transition metal;

the circle represents a mono- or polycyclic system comprising at least two N-heteroatoms;

n is 1-10, preferably 2-6, most preferably 3-4;

X is as defined above for (III).

The cyclic system may, for example, be selected from imidazole, purine, pyrazine, pyrimidine, 1,8-naphthydrin, chinoxaline, chinazoline, pteridine. Preferably, the cyclic system is imidazole, resulting in N-donor ligands comprising structures as illustrated in formula (IV) and (V) below.

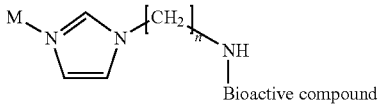

(IV)

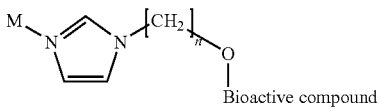

(V)

in which n is as indicated for (III) above.

The bioactive compound comprises, in its released and/or original, active form, a carboxy-group, which is linked to the N-atom or O-atom indicated in (IV) or (V), upon formation of a amide bond.

Examples of P-donor ligands are $PR^{P1}R^{P2}R^{P3}$, in which $R^{P1}$, $R^{P2}$, and $R^{P3}$ are defined as $R^{N1}$, $R^{N2}$, and $R^{N3}$ above, wherein a fused P-donor ligand may arise if two or all three of $R^{N1}$-$R^{N3}$ are fused.

A preferred example of a P-donor ligand is PTA (1,3,5-triaza-7-phospha-adamantane).

S-donor ligands are ligands which bind to M via a sulphur atom. Examples include thiosulfate ($S_2O_3^{2-}$); isothiocyanate (NCS$^-$); sulfoxide ligands ($R^{S1}R^{S2}SO$); thioether ligands ($R^{S1}R^{S2}S$); thiolate ligands ($R^{S1}S^-$); sulfinate ligands ($R^{S1}SO_2^-$); and sulfenate ligands ($R^{S1}SO^-$), wherein $R^{S1}$ and $R^{S2}$ are independently selected from alkyls, alkenyls, alkynyls, aryls, optionally substituted and optionally comprising one or more heteroatoms.

O-donor ligands are ligands which bind to M via an oxygen atom. Examples include carbonate ($CO^{3-}$); carboxylate ligands ($R^C CO^{2-}$); nitrate (NO3$^-$); sulfate ($SO4^{2-}$) and sulphonate ($R^{S1}O3^-$), wherein $R^C$ is selected from alkyls, alkenyls, alkynyls, aryls, optionally substituted and optionally comprising one or more heteroatoms.

According to the organometallic complex of the invention, two, three or more of the ligands $R_1$, $R_2$, $R_3$, $R_4$, $R_5$, $R_6$ may be present in the form of one or more single compounds, the single compound being a bi-, tri- or polydentate compound, and/or, an alkene, alkyne, cyclopentadienyl and/or an arene, the alkene, alkyne, cyclopentadienyl and/or an arene being optionally substituted and optionally comprising one or more heteroatoms.

Bi-, tri- or polydentate ligands generally comprise at least two donor ligands, such as N-, P-, O- or S-donor ligands as defined above, for example. A bi-, tri- or polydentate ligand may, furthermore, comprise different donor ligands within the same compound.

An example of a bidentate N-donor ligand is 2,2'-bipyridine, optionally substituted. An example of a bidentate O-donor ligand is oxalate. A well known example of a polydentate ligand is EDTA (ethylene diamine tetraacetic acid), which comprise 6 donor locations. In this case, all residues $R_1$-$R_6$ would be provided by one single polydentate compound.

Two or more substituents of $R_1$-$R_6$ may be present in the form of one or more single compounds being a alkene, alkyne, cyclopentadienyl, and/or arene.

In these cases, double bonds of the ligands may play a role in the formation of the bond with the central M, thus giving rise, if the ligands are formed by a cyclic compound, to sandwich or half-sandwich ("piano-stool") configurations, for example.

Accordingly, in a preferred embodiment, three ligands of the organometallic compound of the present invention selected from $R_1$, $R_2$, $R_3$, $R_4$, $R_5$, and $R_6$, are present in the form of an alkene, alkyne, cyclopentadienyl and/or arene, optionally substituted and optionally comprising one or more heteroatoms, optionally bound covalently to the bioactive compound.

Examples of linear alkenes that function as suitable ligands to M include alkene, propene, 1,3-butadiene.

Examples of cyclic alkenes that function as suitable ligands to M include cyclohexa-1,4-diene and cycloocta-1,5-diene.

Preferably, three ligands selected from $R_1$-$R_6$ are formed by an organic molecule such as an arene. Preferably, the selected ligands result in a pseudo-octahedral arrangement around a central M, although other geometries are also possible, e.g. pentagonal bipyramid, square pyramid, tetrahedral and square planar or intermediate structures thereof.

The compound of the invention may thus be a half-sandwich compound. Preferably, three ligands selected from $R_1$-$R_6$ are formed by a cyclic alkene, cyclopentadienyl and/or by an arene, optionally substituted, and optionally comprising one or more heteroatoms. The at least one cyclic "tridentate" ligand may be a mono-, bi-, tri- or polycyclic compound. Preferably, it is monocyclic. Preferably, it is an arene. Arenes are aromatic hydrocarbons. They may be substituted and comprise one or more heteroatoms.

Examples of mono-cyclic arenes are benzene and cyclopentadienyl ($C_5H_5^-$). The later is considered by the present inventors being an arene, but is often mentioned explicitly for the sake of avoiding doubts. Examples of monocyclic arenes comprising at least one N-heteroatom are pyridine, pyrazine, pyrimidine, pyridazine, for example. Of course, other heteroatoms may be present in the arene besides or instead of N, such as those mentioned above.

Accordingly, the arene may be polycyclic. Examples of polycyclic arenes are pentalene, indene, naphthalene, azulene, and so forth. Examples of polycyclic arenes comprising N-heteroatoms are indolizine, +H-indole, 2H-isoindole, 3H-indole, 1H-indazole, /H-purine, indoline, isoindoline, 4H-quinolizine, quinoline, isoquinoline, pteridine, phtalizine, naphthydrine, quinazoline, cinnoline. Of course, other heteroatoms may be present in the polycyclic arene besides or instead of N, such as those mentioned above.

Most preferably, the organometallic compound of the present invention comprises, as at least one ligand, at least one are selected, independently, from benzene and cyclopentadienyl, which are optionally substituted by alkyl, alkenyl, alkynyl or aryl residues, optionally further substituted and comprising one or more heteroatoms.

According to a preferred embodiment of the present invention, three adjacent ligands of the organometallic compound of the invention, selected from $R_1$, $R_2$, $R_3$, $R_4$, $R_5$, $R_6$ are formed by an arene of formula (VI)

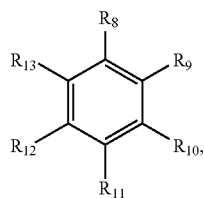

(VI)

in which $R_5$, $R_9$, $R_{10}$, $R_{11}$, $R_{12}$, $R_{13}$ may, independently of each other, be the same or different, are each hydrogen, allyl, alkenyl, alkynyl, or aryl, which are, if applicable, optionally substituted and which optionally comprise one or more heteroatoms, and in which two or more residues selected from $R_8$, $R_9$, $R_{10}$, $R_{11}$, $R_{12}$, $R_{13}$ may be covalently linked with each other thus forming a bi- or tri-, or polycyclic system, and in which any of the residues $R_8$-$R_{13}$ is optionally bound to the bioactive compound.

Monocyclic examples of arenes according to the compound of formula (VI) without heteroatoms are benzene, methylbenzene, cymene, for example.

Monocyclic examples of arenes according to the compound of formula (VI) comprising any one or more residues selected from $R_8$-$R_{13}$ being an alkyl, alkenyl or alkynyl that is substituted and/or comprising at least one heteroatom, the remaining residues being hydrogens are benzyl alcohol, 2-phenylethanol, 3-phenylpropanol, 4-phenylbutanol, benzylamine, 2-phenylethanamine, 3-phenylpropanamine, 4-phenylbutanamine, 2-phenylethanaminium, N,N,-dimethyl-2-phenylethanamine, all of which may be substituted to be bound to the bioactive organic compound.

The residues $R_8$-$R_{13}$ may thus comprise charges, but are preferably non-charged.

One or more residues selected from $R_8$-$R_{13}$ may comprise heteroatoms with electron pairs or double bonds that are linked to the central M, thus forming one of the ligands $R_1$-$R_6$, which is not yet occupied. An example of a compound falling in this category is reproduced by formula (VII) below:

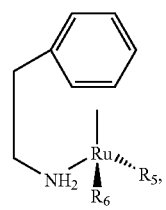

(VII)

in which the bioactive organic compound may be linked to any of residues $R_5$ or $R_6$ or to an optional further residue of the benzene ring.

Examples of bicyclic variants of compound (VI), in which two residues, $R_{12}$ and are $R^{13}$ are covalently inked forming a bicyclic systems are indicated with formulae (VIII) and (IX) below

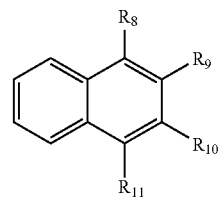

(VIII)

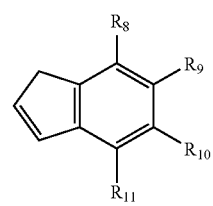

(IX)

in which $R_8$-$R_{11}$ have the same meaning as above in formulae (VI).

Further substituents may be present on the cycle formed by $R_{12}$ and $R_{13}$, which are not shown here.

According to a particularly preferred embodiment of the present invention, the compound of formula (VI) comprises the structure of formula (IX):

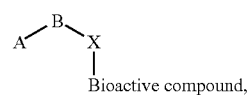

(X)

in which,
A is a optionally substituted, benzyl or cyclopentadienyl,
B is an optional linking group, which may be selected from alkyl, alkenyl, alkynyl and aryl, which is optionally substituted, which optionally comprises one or more heteroatoms and has 0-15, preferably 1-8 carbon atoms;

X is a functional group of B or the cyclic system, through which the bioactive compound is bound to B or to the cyclic system.

Preferably, in (X), A is benzene.

Preferably, in (X), B is a $C_1$-$C_{16}$, more preferably a $C_2$-$C_4$ alkyl. Preferably the alkyl only comprises X as a substituent and is otherwise unsubstituted.

Preferably, X is selected from —O— and from —NH—. Accordingly, X preferably represents ether or part of an ester or amide group, of which the carbonyl part, if applicable, may be part of the "bioactive compound" or of the alkylene. Preferably, the bioactive compound, in its released and/or original, active form, comprises a carboxy-group and is linked to the N- or O-heteroatom indicated as X in formula (X) by means of a amide bond or ester bond, respectively.

Accordingly, in case of an ester bond, a hydroxy group of B may be esterified with a carboxy group of the bioactive compound, or, vice versa, a hydroxy group of the bioactive compound may be esterified with a carboxy-group optionally present on B. Both alternatives allow for hydrolytic cleavage and release of the bioactive compound.

In the case of an amide bond, an amino group of B may be linked to a carboxy group of the bioactive compound, or, vice versa, an amine group of the bioactive compound may be esterified with a carboxy-group optionally present on B. Both alternatives allow for hydrolytic cleavage and release of the bioactive compound.

According to further, particularly preferred embodiments, the compound of formula (VI) comprises the structures of formula (XI) and (XII):

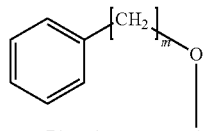

(XI)

Bioactive compound

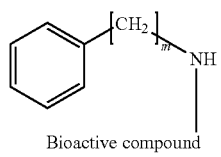

(XII)

Bioactive compound in which,
m is 1-10, preferably 2-8.

Preferably, —O— and —NH— represent ester and peptide bonds, respectively, as defined for X in formula (X above. More preferably, the bioactive compound, in its released and/or original, active form, comprises a carboxy-group and is linked to the O- or the N-atom indicated in (XI) and (XII), respectively, by means of an ester and peptide bond, respectively.

Most preferably, m in formula (XI) is 1 and in (XII) is 2.

According to a preferred embodiment, at least one of $R_1$, $R_2$, $R_3$, $R_4$, $R_5$, $R_6$ of the organometallic compound of the present invention is a residue suitable of increasing the solubility of the complex of formula (I) in water ($H_2O$). This residue is preferably selected specifically for this purpose. The bioactive organic compound may be linked to this residue. Generally, hydrocarbons having a high heteroatom:carbon ratio are suitable to increase the solubility.

Accordingly, at least one of the residues $R_1$-$R_6$ has the purpose of increasing the solubility of the organometallic compound of the invention in water. Preferably, the at least one ligand has a hydrophilic group. Hydrophilic groups include (—OH), (═O), (—COOH), (—NH$_2$), (—NHR—), (—O—), (—SH$_2$), (—S—), (—SO$_3$—), for example, with R being optionally substituted alkyl, alkenyl or aryl.

For example, the at least one residue selected from $R_1$-$R_6$ for increasing solubility in water may be a hydrocarbon comprising one or several groups capable of engaging in hydrogen bonding with water, such as, for example, hydroxy groups.

In a preferred embodiment of the organometallic compound of the present invention, at least one organometallic compound of claim 1, in which any of $R_1$, $R_2$, $R_3$, $R_4$, $R_5$, $R_6$ has the formula (XIII), $$P\ R_{14}R_{15}R_{16} \qquad (XIII),$$

in which, $R_{14}$, $R_{15}$, $R_{16}$ may be the same or different, are each $C_1$-$C_6$ alkyl, aryl or substituted aryl, or $R_{14}$, $R_{15}$, $R_{16}$ may together with the phosphorous atom form a cycloalkyl group, such group being optionally heterocyclic. Preferably, $R_{14}$, $R_{15}$, $R_{16}$ together form a fused ring system comprising 1-5 heteroatoms, preferably N. This residue, if present, preferably increases the solubility of the organometallic compound of the present invention in water.

An example of a residue capable of increasing solubility is 1,3,5-triaza-7-phospha-adamantane (PTA), 3-methyl-1,3,7-triaza-5-phosphabicyclo[3.3.1]nonane (MePTA), 3,7-diacetyl-1,3,7-triaza-5-phosphabicyclo[3.3.1]nonane (DAPTA), which may be linked via the P-atom to the central M in the compound of the present invention. An example of a bivalent ligand capable of increasing solubility of the compound of the present invention in water is oxalate.

In a preferred embedment the organometallic compound of the present invention comprises the structure (XIV) below,

(XIV)

in which,

A is an arene, optionally substituted and optionally comprising one or more heteroatoms;

$R_{18}$, $R_{19}$, $R_{20}$, are ligands of the central Ruthenium atom which are, independently of each other, selected from halogens and/or N-, O-, S-, or P-donor ligands;

$R_{17}$ is an optional residue selected from an alkyl, alkenyl, alkynyl, aryl, optionally substituted and optionally comprising one or more heteroatoms;

whereby the at least one bioactive organic compound constitutes at least one selected from $R_{17}$-$R_{20}$, or is covalently linked to any of the $R_{17}$-$R_{20}$, with the proviso that residues selected from $R_{17}$-$R_{20}$, which constitute the bioactive organic compound, or which are covalently bound the bioactive organic compound, are not halogens.

Preferred A and residues $R_{17}$-$R_{20}$ are as indicated above. Accordingly, the grouping of A-$R_{17}$ may be selected from formulae (X)-(XII), and the residues $R_{18}$-$R_{20}$, may be selected from halogens mentioned above and from N—, O—, S—, or P-donor ligands mentioned above, for example. If the bioactive compound is bound to one or more of $R_{18}$-$R_{20}$, this/these residue(s) may be selected from formulae (III)-(V), for example.

According to a still preferred embodiment, the organometallic compounds of the present invention comprise the structures (XV) below:

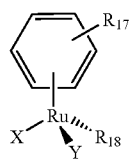

(XV)

in which,
X is a halogen;
Y is a halogen or N-, P-, O- or S-donor ligand as defined above; and,
in which,
if the bioactive compound is bound to $R_{17}$, $R_{17}$ is corresponds to "B—X—" as defined in formula (X) above, and $R_{18}$ is a N-, P-, O- or S-donor ligand as defined above; and/or,
if the bioactive compound is bound to $R_{18}$, or constitutes $R_{18}$, $R_{19}$ is, respectively, a N-, P-, O- or S-donor ligand as defined above to which the bioactive compound is covalently bound; or
$R_{18}$ constitutes the bioactive compound, the bioactive compound comprising itself N-, P-, O- or S-atoms functioning as donors suitable to attach it to the central Ru.

Preferably, Y in (XV) is a halogen.
Preferably, $R_{18}$ is P $R_{14}R_{15}R_{16}$ as defined above. Preferably, it is PTA.

Preferably, in (XV), the bioactive compound is linked to $R_{17}$ by a amide or ester bond. For example, the benzene to which $R_{17}$ is bound, $R_{17}$ and the bioactive compound together may correspond to the structure illustrated in formulae (XI) and (XII), for example.

If the bioactive compound is linked to $R_{18}$, $R_{18}$ and the bioactive compound preferably correspond to any of formula (II)-(V) above.

If the bioactive compound is linked to $R_{18}$, $R_{18}$ is preferably a N—, P—, O—, or S-donor ligand, to which the bioactive compound is linked. Accordingly, $R_{18}$ preferably carries a functional group to which the bioactive compound can be linked, such as amide and ester bonds, as mentioned above.

In this alternative case, with $R_{18}$ being covalently bound to the bioactive compound, $R_{17}$ may represent one or more residues such as $R_8$-$R_{13}$ in the compound of formula (VI) above.

The present invention also envisages the possibility that the organometallic compound comprises more than one bioactive compound covalently bound to a ligand selected from $R_1$-$R_6$. Accordingly, in the above example of formula (XV), both, $R_{17}$ and $R_{18}$ may be covalently bound to a bioactive organic compound, whereby $R_{18}$ may, instead constitute the bioactive compound. The bioactive compounds may then be the same or different. It they are different, the second bioactive compound may have a biological activity different from the bioactive compound generally used in the context of the present invention. Preferably, however, if more than one bioactive compounds are present, all are useful in the treatment of cancer in general and/or metastasis in particular.

Many residues, and in particular ligands attached to M detailed above are indicated to be substituted. For the purpose of the present invention, substituents are preferably selected, independently from each other if there are more than one substituents, from alkyls, alkenyls, alkynyls, aryls, the alkyls, alkenyls, alkynyls, aryls, optionally comprising one or more heteroatoms, and functional groups such as, for example, imine-groups (=NH), amino groups (—NH$_2$), hydroxy groups (—OH), thiol groups (—SH), carbonyl groups (=O), thio groups (=S), carboxyl groups (—COOH), nitrile groups (—C≡N), nitro groups (—NO$_2$), any other functional group and, if applicable, charged derivatives (for example, if pH dependent) and salts of the functional groups, for example. The substituent comprising a functional group may be substituted at the functional group.

Substituents may be branched and/or be further substituted.

The present invention, for example in claim 1, refers to an alkene, alkyne, cyclopentadienyl, and/or arene. The alkene or alkyne is considered to be an unsaturated $C_2$-$C_{30}$, more preferably a $C_3$-$C_{15}$ and most preferably $C_4$-$C_8$ hydrocarbon. An alkene comprises at least one (C=C)-double bound, whereas the alkyne comprises at least one (C≡C)-triple bond. The arene is preferably an aromatic $C_5$-$C_{35}$, more preferably $C_6$-$C_{20}$, most preferably $C_6$-$C_{15}$ hydrocarbon. The alkene or alkyne may also be cyclic, if there are ≥3 carbons. The alkene or alkyne may be branched, if there are ≥4 or ≥5 carbons, respectively. The alkene, alkyne, cyclopentadienyl and/or arene (or aryl radical) may further be substituted, as indicated above, and optionally comprising one or more heteroatoms.

Alkenyl, alkynyl and/or aryl residues or substituents, as mentioned, for example, with respect to nitrile and azo ligands, aromatic N-donor ligands, amine ligands, P-donor ligands, S-donor ligands, O-donor ligands, substituents of benzene or cyclopentadienyl ligands, substituents selected from $R_8$-$R_{13}$, $R_{17}$ in formula (III), substituents of the alkene, alkyne, cyclopentadienyl and/or arene mentioned in the above paragraph, substituents of an alkyl or with respect to substituents in general are radicals of the alkenes, alkynes, cyclopentadienyls and/or arenes as defined in the paragraph above.

Alkyl substituents, as mentioned, for example, with respect to substituents in general as defined above, N-donor ligands, in particular nitrile and azo ligands, aromatic N-donor ligands, amine ligands, substituents of B in formula (II), P-donor ligands, S-donor ligands, O-donor ligands, substituents of the alkene, alkyne and/or arene of claim 1, substituents of benzene and/or cyclopentadienyl, substituents $R_8$-$R_{13}$ of formulae (VI), substituents of B in formula (IX), substituents selected from $R_{14}$-$R_{15}$, $R_{17}$ in formula (III), are preferably $C_1$-$C_{30}$ alkyls, more preferably $C_2$-$C_{25}$ alkyls, even more preferably $C_4$-$C_{10}$ alkyls. If the alkyl comprises more than 3 carbons, it may be cyclic or branched. Alkyls that are cyclic and branched are also encompassed, if the comprise more than 6 carbons. Alkyls may generally be further substituted.

A heteroatom, for the purpose of the present invention may be any heteroatom, but is preferably selected from B, Si, N, P, As, O, S, Se, T, and halogens. If several heteroms are present, they may be the same or different. More preferably, heteroatoms are selected from N, O, P, S, and halogens. If the heteroatom is present in a substituent, alkene, alkyne, cyclopentadienyl or arene, it may change the chemical class of the compound. For example, an O present in a linear alkyl results in an ether. For the purpose of the present invention, this example would be considered to be an alkyl comprising one O heteroatom.

The present invention provides an organometallic compound having a bioactive agent linked to at least one of the ligands of the central M.

Preferably, the bioactive organic compound is selected from inhibitors of resistance pathways and/or a pharmaceutically acceptable derivatives thereof. Inhibiting activity may, if it is not yet described, be assessed by specific, commercially obtainable or described assays. The skilled person is capable of using meaningful concentrations of an presumed inhibitor in such an assay. An example of an assay for testing Glutathione S-transferase inhibiting activity is mentioned in Example 6.

According to a preferred embodiment, the bioactive organic compound is an inhibitor of resistance selected from Glutathione S-transferase (GST) inhibitors, γ-Glutamyl Cysteine Synthetase (γ-GCS) inhibitors, multidrug resistance protein (MRP)/P-glycoproteins (PgP) inhibitors, inhibitors of cell signalling pathways.

Examples of inhibitors of Glutathione S-transferase inhibitors comprise, but not limited to, ethacrynic acid, peptidomimetics based on gluthatione, p-chlorophenoxyisobutyrate, Gossypol indomethacin, non-steroidal anti-inflammatory compounds based on ibuprofen and ketoprofen, misonidazole, Piriprost, Sulfasalazine, and their derivatives.

Examples of inhibitors of γ-Glutamyl Cysteine Synthetase comprise, but not limited to, sulfoxime-based compounds such as buthinone sulfoxime and methinone sulfoxime, S-sulfocysteine, S-sulfohomocysteine, cystamine, and their derivatives.

Examples of inhibitors of the multidrug resistance protein comprise, but not limited to, quinidine, vinblastine, terfernadine, tamoxifen, verapamil, cyclosporin, amitriptyline, progesterone, and their derivatives.

Examples of inhibitors of cell signaling pathways comprise, but not limited to, pleurotin, azelaic acid, bischloroethylnitrosourea, palmarumycin, and their derivatives.

Optically pure enantiomers, mixtures of enantiomers such as racemates, diastereomers, mixtures of diastereomers, diastereomeric racemates, mixtures of diastereomeric racemates, and the meso-form, as well as pharmaceutically acceptable salts, solvent complexes and morphological forms of the bioactive organic compounds are also encompassed by the present invention.

The expression pharmaceutical acceptable derivatives and derivatives also encompasses, but is not limited to, salts.

Salts comprise, for example, salts with inorganic acids or organic acids like hydrochloric or hydrobromic acid, sulphuric acid, phosphoric acid, citric acid, formic acid, acetic acid, maleic acid, tartaric acid, benzoic acid, methanesulfonic acid, p-toluenesulfonic acid, and the like that are non toxic to living organisms or in case the compound (I) is acidic in nature with an inorganic base like an alkali or earth alkali base, e.g. sodium hydroxide, potassium hydroxide, calcium hydroxide and the like.

According to the present invention, the bioactive compound constitutes a ligand of the central M selected from $R_1$-$R_6$, or is covalently bound to a ligand to the central M of the organometallic compound of the invention. If the bioactive compound is covalently bound to the ligand, the covalent bond can be a carbon-carbon alkyl, alkenyl or alkynyl bonds, or carbon-heteronuclear bonds such as amide (—CONH—), ester (—$CO_2$—), ether (—$CH_2O$—), thioether (—$CH_2S$—), amine (—$CH_2N$—), imine (—CH=N—), phosphorous (—$CH_2P$—). Preferably, the covalent bond is a carbon heteronulcear bond.

According to a preferred embodiment of the present invention, the organometallic compounds of the present invention are used as medicaments.

More particularly, according to a preferred embodiment, the organometallic compound according to any of the preceding claims in the treatment and/or prevention of cancer and/or metastasis. The effectiveness of the present compounds for the treatment of metastasis is remarkable. With many cancers, tumors may be removed surgically, with the occurrence of metastasis remaining the principle problem to which so far no convincing remedy has been found. Surprisingly, the compounds of the present invention are effective in overcoming the resistance of many cancer cells in metastasis to anti-cancer drugs. Thanks to the compounds of the present invention, anti-cancer drugs that are inefficient due to the onset of resistance against it, these very drugs may again be effectively employed. In addition, due to the increase of efficiency against cancer drugs, lower doses of the later may be applied, thus reducing the occurrence and severity of side effects.

Accordingly, according to a preferred embodiment, the organometallic compound according to the invention are useful for reducing resistance of cancers and/or metastasis against anti-cancer drugs.

According to a further embodiment, the present invention comprises a composition comprising an anti-cancer drug and the organometallic compound of any of the preceding claims for treating and/or preventing metastasis. The organometallic compound of the invention is most effective if administered together with an anti-cancer drug which may be conventional, and to which cancer cells have developed resistance, or a capable of developing resistance.

As becomes clear from the above, the principle of the present invention does not only encompass a single, specific compound but is more general. In particular, with respect to the different ligands bound to the central M, and to one of which the bioactive compound is covalently bound, a large variability is provided. The bioactive compound may also be directly attached to the central atom, increasing the variability. If the bioactive compound is bound to a ligand, it may be linked to ligands of different general structure and to ligands that are linked to the central M in different ways, for example as free-electron-pair-donors or as donors of π-bonds that are capable of complexing or associating to a transition metal. Preferably, however, the central M is Ruthenium (Ru), and the overall compound has a sandwich or half-sandwich structure.

Therefore, a high variability exists with respect to the ligands. For examples, the arene-part shown in exemplary ligands of formula (VII) and (VIII) may be selected from a large number of possible arenes that can be used in sandwich- or half-sandwich compounds. These arenes may, of course, be substituted, for example for improving the physico-chemical properties of the overall compound, such as solubility, or for improving effectiveness and reducing toxicity to normal cells. Such substituents are not shown here in all the detail, they may be selected at the discretion of the skilled person and are not essential for the general principle described herein.

The following examples illustrate the principle of the present invention on the basis of ethacrynic acid, which functions as the bioactive compound and which is shown to be effective in the treatment of metastasis. The examples also illustrate the structural variably of connecting the bioactive compound to ligands of different structures and being linked to the central M in different ways.

A. EXAMPLES 1-5

Synthesis of the Organometallic Compounds of the Invention

Example 1

Ethacrynic-(cyclohexa-1,4-dienyl)methylamide (1)
Ethacrynic acid (500 mg, 1.65 mmol) was refluxed in oxalyl chloride (5 ml) for 30 mins. Unreacted oxalyl chloride was removed in vacuo and dichloromethane (10 ml) was added to redissolve the residual colourless oil. (cyclohexa-1,4-dienyl)methamine (109 mg, 1.00 mmol) and triethylamine (1 ml) was added sequentially and the reaction mixture was refluxed for a further 6 h On completion, a dark brown solution was obtained. The reaction mixture was washed with 5% $NaHCO_3$ (50 ml), brine (2×50 ml) and dried in vacuo. The residual oil was separated on silica using 5:95 MeOH:dichloromethane as the eluent to yield a colourless oil which crystallizes on standing (yield: 250 mg, 63.3%). $^1$H NMR ($CDCl_3$, 400.13 MHz) 7.19 (d, 1H, $Ar_{EA}$-H, $^3J_{HH}$=8.4 Hz), 6.87 (d, 1H, $Ar_{EA}$-H, $^3J_{HH}$=8.4 Hz), 6.81 (b, 1H, —$CH_2NH$—), 5.95 (s, 1H, =$CH_2$), 5.64-5.71 (m, 3H, C=CH—C), 5.58 (s, 1H, =$CH_2$), 4.60 (s, 2H, —$OCH_2CO_2$—), 3.91 (d, 2H, —$CH_2NH$—, $^3J_{HH}$=6.0 Hz), 2.83 (t, 2H, —$CH_2NH$—, $^3J_{HH}$=6.0 Hz), 2.61-2.72 (m, 4H, =$CH_2$—C—), 2.47 (q, 2H, —$CH_2CH_3$, $^3J_{HH}$=7.6 Hz), 1.15 (t, 3H, —$CH_2CH_3$, $^3J_{HH}$=7.6 Hz).

[(Ethacrynic-$\eta^6$:benzylamide)RuCl($\mu$-Cl)]$_2$ (2)

(1) (0.43 g, 3.32 mmol) was refluxed with $RuCl_3.3H_2O$ (50 mg, 0.192 mmol) in degassed EtOH (25 ml) for 6 hours and left to stand at −4° C. for 12 h, during which a reddish-orange precipitate separates from the dark green solution. The precipitate was filtered, dissolved in dichloromethane and precipitated using diethyl ether to yield a light orange precipitate. The product was dried in vacuo (yield: 76.0 mg, 70.4%). $^1$H NMR ($CDCl_3$, 400.13 MHz) 8.11 (t, 1H, —$CH_2NH$—), 7.16 (d, 1H, $Ar_{EA}$-H, $^3J_{HH}$=8.4 Hz), 6.90 (d, 1H, $Ar_{EA}$-H, $^3J_{HH}$=8.4 Hz), 5.97 (s, 1H, =$CH_2$), 5.77 (t, 1H, p-$Ar_{Ph}$-H, $^3J_{HH}$=6.0 Hz), 5.63 (s, 1H, =$CH_2$), 5.56 (dd, 2H, m-$Ar_{Ph}$-H, $^3J_{HH}$=6.0, 6.0 Hz), 5.43 (d, 2H, o-$Ar_{Ph}$-H, $^3J_{HH}$=6.0 Hz), 4.80 (s, 2H, —$OCH_2CO_2$—), 4.58 (d, 2H, —$CH_2NH$—, $^3J_{HH}$=6.0 Hz), 2.47 (q, 2H, —$CH_2CH_3$, $^3J_{HH}$=7.6 Hz), 1.15 (t, 3H, —$CH_2CH_3$, $^3J_{HH}$=7.6 Hz). Anal. ($C_{40}H_{38}Cl_8N_2O_6Ru_2$) C, 42.57; H, 3.39; N, 2.48. Found C, 42.48; H, 3.52; N, 2.70.

(Ethacrynic-$\eta^6$:benzylamide)Ru(PTA)Cl$_2$ (3)

(2) (28.4 mg, 0.025 mmol) was refluxed with PTA (9.3 mg, 0.059 mmol) in 1:1 MeOH/dichloromethane (15 ml) for 2 hours. The solvent was removed and the residual was recrystallised from dichloromethane/diethyl ether to yield and an orange precipitate (yield: 31 mg, 85.3%). $^1$H NMR ($CDCl_3$, 400.13 MHz) 7.87 (t, 1H, —$CH_2NH$—), 7.18 (d, 1H, $Ar_{EA}$-H, $^3J_{HH}$=8.4 Hz), 6.90 (d, 1H, $Ar_{EA}$-H, $^3J_{HH}$=8.4 Hz), 5.96 (s, 1H, =$CH_2$), 5.07 (t, 1H, p-$Ar_{Ph}$-H, $^3J_{HH}$=5.6 Hz), 5.60 (s, 1H, =$CH_2$), 5.70 (m, 2H, m-$Ar_{Ph}$-H), 5.52 (d, 2H, o-$Ar_{Ph}$-H, $^3J_{HH}$=6.0 Hz), 4.69 (s, 2H, —$OCH_2CO_2$—), 4.56 (d, 2H, —$CH_2NH$—, $^3J_{HH}$=6.0 Hz), 4.51 (s, 6H, PTA-N—$CH_2$—N), 4.32 (s, 6H, PTA-P—$CH_2$—N), 2.47 (q, 2H, —$CH_2CH_3$, $^3J_{HH}$=7.6 Hz), 1.15 (t, 3H, —$CH_2CH_3$, $^3J_{HH}$=7.6 Hz). Anal. ($C_{26}H_{31}Cl_4N_4O_3PRu$) C, 42.23; H, 4.50; N, 7.58. Found C, 42.54; H, 4.40; N, 7.74.

Example 2

(Ethacrynic-$\eta^6$:phenylethanoate)Ru(PTA)Cl$_2$ (4)

Ethacrynic acid (200 mg, 0.66 mmol), N,N-dicyclohexylcarbodiimide (200 mg, 0.98 mmol), N,N-diethylaminopyridine (120 mg, 1.10 mmol) and ($\eta^6$:phenylethanol)Ru(PTA)Cl$_2$) (90 mg, 0.20 mmol) was dissolved in dichloromethane (50 ml) and stirred for 96 h. The reaction mixture was filtered through celite to remove the urea precipitate and separated on silica gel using acetone. The product was triturated in diethyl ether and recrystallised from dichloromethane/diethyl ether to yield a brown precipitate (yield: 50 mg, 34.0%). $^1$H NMR ($CDCl_3$, 400.13 MHz) 7.07 (d, 1H, $Ar_{EA}$-H, $^3J_{HH}$=8.4 Hz), 6.72 (d, 1H, $Ar_{EA}$-1H, $^3J_{HH}$=8.4 Hz), 6.00 (s, 1H, =$CH_2$), 5.62 (s, 1H, =$CH_2$), 5.48 (m, 2H, m-$Ar_{Ph}$-H), 5.22 (d, 2H, o-$Ar_{Ph}$-H, $^3J_{HH}$=5.6 Hz), 5.13 (t, 1H, p-$Ar_{Ph}$-H. $^3J_{HH}$=5.2 Hz), 4.81 (s, 2H, —$OCH_2CO_2$—), 4.55 (s, 6H, PTA-N—$CH_2$—N), 4.50 (t, 2H, —$CO_2CH_2CH_2$—, $^3J_{HH}$=6.0 Hz), 4.33 (s, 6H, PTA-P—$CH_2$N), 2.83 (t, 2H, —$CO_2CH_2CH_2$, $^3J_{HH}$=6.0 Hz), 2.47 (q, 2H, —$CH_2CH_3$, $^3J_{HH}$=7.6 Hz), 1.16 (t, 3H, —$CH_2CH_3$, $^3J_{HH}$=7.6 Hz). Anal. ($C_{27}H_{32}Cl_4N_3O_4PRu$) C, 44.03; H, 4.38; N, 5.71. Found C, 43.94; H, 4.40; N, 5.72.

Example 3

N-[2-(1H-imidazol-1-yl)propyl]ethacrynic-amide (5)

Ethacrynic acid (349 mg, 1.16 mmol) was refluxed in dichloromethane (20 ml) with an excess of oxalyl chloride (2 ml) for 1 h. Unreacted oxalyl chloride was removed under vacuum and the reaction mixture concentrated to yield ethacrynic acid chloride as a colourless oil. The acid chloride was taken up in dichloromethane (20 ml) and N-aminopropyl)imidazole (500 mg, 4.00 mmol) was added. The reaction mixture was then refluxed for 2 h. 5% $NaHCO_3$ solution (25 ml) was added to quench the reaction and the aqueous phase was extracted with dichloromethane (3×25 ml). The organic phases were combined and washed with brine (2×25 ml) and dried over $Na_2SO_4$. The solvent was removed and the product was separated on silica using 20% EtOH/80% $CHCl_3$. The solvent was removed to yield a colourless oil (yield: 378 mg, 79.5%). $^1$H NMR ($CDCl_3$, 400.13 MHz) 7.52 7.07 6.96 (s, 3H, $Ar_{imdazole}$-H), 7.20 6.86 (d, 2H, $Ar_{EA}$-H, $^3J_{HH}$=8.4 Hz), 6.82 (m, 1H, NH), 5.96 5.59 (s, 2H, =$CH_2$), 4.57 (s, 2H, —$OCH_2CO_2$—), 4.04 (t, 2H, Im-$CH_2$—$CH_2$), 3.42 (dt, 2H, $CH_2$—$CH_2NH$), 2.47 (q, 2H, —$CH_2CH_3$, $^3J_{HH}$=7.6 Hz), 2.10 (tt, 2H, $CH_2$—$CH_2$—$CH_2$), 1.16 (t, 3H, —$CH_2CH_3$, $^3J_{HH}$=7.6 Hz).

($\eta^6$-cymene)RuCl$_2$(ethacrynic-propylamide-imidazole) (6)

[($\eta^6$-cymene)RuCl($\mu$-Cl)]$_2$ (68 mg, 0.11 mmol) and (5) (94 mg, 0.23 mmol) was dissolved in dichloromethane (25 ml) and stirred for 12 h. The reaction mixture was concentrated and pentane was added to precipitate the product. The product was recrystallised from dichloromethane/pentane to yield an orange precipitate (yield: 144 mg, 90.3%). $^1$H NMR ($CDCl_3$, 400.13 MHz) 7.95 7.30 6.91 (s, 3H, imidazole-H), 7.19 6.90 (d, 211, $Ar_{EA}$-H, $^3J_{HH}$=8.4 Hz), 6.94 (t, 1H, N—H), 5.96 5.61 (s, 2H, =$CH_2$), 5.45 5.26 (dd, 4H, $Ar_{Ph}$-H, $^3J_{HH}$=6.0 Hz), 4.60 (s, 2H, —$OCH_2CO_2$—), 3.89 (t, 2H, —$CH_2CH_2$-imidazole, $^3J_{HH}$=7.2 Hz) 3.36 (q, 2H, $NHCH_2CH_2$—, $^3J_{HH}$=7.2 Hz), 2.96 (septet, 1H, —$CH_3CHCH_3$, $^3J_{HH}$=8.0 Hz), 2.47 (q, 2H, —$CH_2CH_3$, $^3J_{HH}$=7.6 Hz), 2.16 (s, 3H, —$ArCH_3$), 1.93 (m, 2H, $NHCH_2CH_2$—), 1.26 (d, 6H, —$CH(CH_3)_2$, $^3J_{HH}$=8.0 Hz), 1.15 (t, 3H, —$CH_2CH_3$, $^3J_{HH}$=7.6 Hz). Anal. ($C_{29}H_{35}Cl_4N_3O_3Ru$) C, 48.67; H, 4.93; N, 5.88. Found C, 48.75; H, 4.95; N, 5.79.

Example 4

[($\eta^6$-cymene)RuCl(PTA)(imidazolium-ethacrynic aide)] $BF_4^-$ (7)

($\eta^6$-cymene)Ru(PTA)Cl$_2$ (96 mg, 0.21 mmol), $NaBF_4$ (92 mg, 0.84 mmol) and (5) (124 mg, 0.30 mmol) was suspended in methanol (15 ml) and refluxed for 2 h, during which a yellow solution was obtained. The reaction mixture was cooled to room temperature and the solvent removed. The residue was extracted with dichloromethane (2×25 ml) and filtered through celite. The dichloromethane extracts was concentrated and diethyl ether was added to precipitate the product. The product was recrystallised from dichloromethane/diethyl ether to yield a yellow precipitate (yield: 150 mg, 77.2%). $^1$H NMR (CDCl$_3$, 400.13 MHz) 8.28 7.42 7.04 (s, 3H, imidazole-H), 7.22 (t, 1H, N—H), 7.17 6.99 (d, 2H, Ar$_{EA}$-H, $^3J_{HH}$=8.4 Hz), 5.96 5.58 (s, 2H, =CH$_2$), 5.81 5.61 (dd, 4H, Ar$_{Ph}$-R), 4.72 (m, 2H, —OCH$_2$CO$_2$—), 4.41 (m, 6H, PTA-N—CH$_2$—N), 4.10 (m, 6H, PTA-P—CH$_2$—N), 3.89 (t, 2H, —CH$_2$CH$_2$-imidazole, 3J$_{HH}$=7.2 Hz) 3.36 (q, 2H, NHCH$_2$CH$_2$—, $^3J_{HH}$=7.2 Hz), 2.96 (septet, 1H, —CH$_3$CHCH$_3$, $^3J_{HH}$=8.0 Hz), 2.47 (q, 2H, —CH$_2$CH$_3$, $^3J_{HH}$=7.6 Hz), 2.16 (s, 3H, —ArCH$_3$), 1.93 (m, 2H, NHCH$_2$CH$_2$—), 1.26 (d, 6H, —CH(CH$_3$)$_2$, $^3J_{HH}$=8.0 Hz), 1.15 (t, 3H, —CH$_2$CH$_3$, $^3J_{HH}$=7.6 Hz). ESI-MS (CH$_2$Cl$_2$, +ve mode) m/z 840 [M]$^+$. Anal. (C$_{35}$H$_{47}$BCl$_3$F$_4$N$_6$O$_3$PRu) C, 45.45; H, 5.12; N, 9.09. Found C, 45.60; H, 5.15; N, 9.07.

Example 5

($\eta^6$ cymene)Ru(PTA)(C$_2$O$_4$) (8)

[($\eta^6$-cymene)RuCl($\mu$-Cl)]$_2$ (196.8 mg, 0.322 mmol) and silver oxalate (240 mg, 0.797 mmol) were stirred in water for 12 h. The mixture was then filtered through celite to remove the AgCl precipitate. The solvent was removed under vacuum and the residue was redissolved in methanol (25 ml). PTA (120 mg, 0.764 mmol) was added and the reaction was stirred for 2 h. The solvent was reduced to ca. 5% of its original volume and diethyl ether (25 ml) was added. The slurry was cooled to 4° C. for 12 h to complete precipitation of the product. The precipitate was filtered and recrystallised from methanol-diethyl ether to yield a light orange precipitate (yield: 285 mg, 89%). $^1$H NMR (D$_2$O, 400.13 MHz) 5.98 5.89 (dd, 4H, Ar—H), 4.57 (s, 6H, PTA-N—CH$_2$—N), 4.15 (5, 6H, PTA-P—CH$_2$—N), 2.61 (septet, 1H, —CH(CH$_3$)$_2$), 2.05 (s, 3H, —CH$_3$), 1.22 (d, —CH(CH$_3$)$_2$). $^{13}$C-{$^1$H} NMR (D$_2$O, 100.63 MHz) 166.2 (—CO$_2$), 105.0 97.7 87.3 86.8 (Ar—C), 70.7 (N—CH$_2$—N), 48.7 (P—CH$_2$—N), 30.8 (—ArCH$_3$), 21.5 (—CH(CH$_3$)$_2$), 17.3 (—CH(CH$_3$)$_2$). $^{31}$P-{$^1$H} NMR (D$_2$O, 400.13 MHz)-33.39. Anal. (C$_{18}$H$_{26}$N$_3$O$_4$PRu.0.5H$_2$O) C, 44.08; H, 5.55; N, 8.57. Found C, 44.24; H, 5.58; N, 8.69.

($\eta^6$-cymene)Ru(PTA)(C$_6$H$_6$O$_4$) (9)

[($\eta^6$-cymene)RuCl($\mu$-Cl)]$_2$ (228 mg, 0.373 mmol) and silver 1,1-cyclobutanedicarboxylate (300 mg, 0.838 mmol) were stirred in acetonitrile (50 ml) for 12 h, during which a yellow precipitate was formed. The solvent was removed and the residue was redissolved in methanol (25 ml). The mixture was filtered through celite to remove the AgCl precipitate. PTA (130 mg, 0.828 mmol) was added to the filtrate and the solution was stirred for 2 hours. The solvent was reduced to ca 5% of its original volume and diethyl ether (25 ml) was added. The slurry was cooled to 4° C. for 4 hours to complete precipitation of the product. The precipitate was filtered and recrystallised from dichloromethane-diethyl ether to yield an orange precipitate (yield: 288 mg, 72.2%). $^1$H NMR (CDCl$_3$, 400.13 MHz) 5.54 5.43 (dd, 4H, Ar—H), 4.49 (s, 6H, PTA-N—CH$_2$—N), 4.15 (s, 6H, PTA-P—CH$_2$—N), 2.76 2.66 (t, 4H, —CH$_2$(CH$_2$)$_2$), 2.58 (septet, 1H, —CH(CH$_3$)$_2$), 2.02 (s, 3H, —CH$_3$), 1.94 (quintet, 2H, —CH$_2$(CH$_2$)$_2$), 1.24 (d, —CH(CH$_3$)$_2$). $^{13}$C-{$^1$H} NMR (CDCl$_3$, 100.63 MHz) 178.7 (—CO$_2$), 102.5 96.1 87.9 85.3 (Ar—C), 72.9 N—CH$_2$—N), 50.8 (P—CH$_2$—N), 30.9 (—(O$_2$C)C(CH$_2$)$_2$), 30.9 (C(CH$_2$)$_{top}$CH$_2$), 30.9 (C(CH$_2$)$_{bottom}$CH$_2$), 30.9 ((—CH$_2$)$_2$CH$_2$), 30.9 (—ArCH$_3$), 22.5 (—CH(CH$_3$)$_2$), 17.3 (—CH(CH$_3$)$_2$). $^{31}$P-{$^1$H} NMR (CDCl$_3$, 400.13 MHz)-30.16. Anal. (C$_{22}$H$_{32}$N$_3$O$_4$PRu.H$_2$O) C, 47.73; H, 6.19; N, 7.59. Found C, 47.99; H, 6.45; N, 7.72.

B. EXAMPLES 6-9

In Vitro and In Vivo Biological Data

Example 6

Determination of Inhibition of Glutathione-S-Transferase Activity

Human A549 lung carcinoma cells, known to express high levels of Glutathione-S-Transferase, were routinely grown in flasks with DMEM medium containing 4.5 g/l glucose, 10% foetal calf serum (FCS) and antibiotics at 37° C. and 6% CO$_2$. When the cells are confluent, they are trypsinised and concentrated in a centrifuge at 4° C. The cells were then diluted in phosphate-buffer saline (PBS) containing protease inhibitor cocktail (final concentration of 1 µg/ml) and homogenised by repeatedly freezing in liquid nitrogen and thawing (4 cycles). The homogenised cell samples were centrifuged at 4° C. and the supernatant, which is the cell lysates, was separated. The cell lysates are stored at −56° C.

The Ru compounds are weighed, and dissolved in DMSO to 100 mM. They are diluted in water to 100 µM such that the DMSO concentration did not exceed 0.1%. The cell lysates were exposed to the drug solutions for 90 mins. Control, containing the cell lysates with water/0.1% DMSO was also prepared.

The GST activity in the treated cell lysates was determined using the glutathione-CDNB (1-chloro-2,4-dinitrobenzene) assay. Glutathione and CDNB were dissolved in deionised water and ethanol respectively to make up a 100 mM solutions. A developing solution, containing 50 mM phosphate buffer solution (pH 6.5), was prepared and was added 1% v/v, the 100 mM glutathione and 100 mM CDNB solutions such that their final concentrations are both 1 mM. The developing solution was added to a 96-well plate at 200 µl per well, followed by the treated cell lysates at 2 µl per well. The absorbance at 340 nm was monitored continuously for 5 mins at 15 s intervals. The average slope of the change in absorbance was determined as a fraction of the control as the percentage of residual GST activity.

Results:

Cells lysates treated with complexes with good GST-inhibition ability should exhibit low residual GST activity. The summary of the results are shown in Table 1 below:

TABLE 1

GST activity in lung carcinoma cells

| Teatment | Residual GST activity (% control) |
|---|---|
| Ethacrynic acid | 86.32 ± 13.5 |
| (Ethacrynic-$\eta^6$: phenylmethylamide)Ru(PTA)Cl$_2$ (3) | 63.57 ± 2.0 |
| (Ethacrynic-$\eta^6$: phenylethanol ester)Ru(PTA)Cl$_2$ (4) | 42.77 ± 13.9 |
| ($\eta^6$-cymene)RuCl$_2$(ethacrynic-propylamide-imidazole) (6) | 23.70 ± 10.7 |
| [($\eta^6$-cymene)RuCl(PTA)(ethacrynic-propylamide-imidazole)]BF$_4^-$ (7) | 62.58 ± 8.8 |

Example 7

Determination of Cell Growth Proliferation Inhibition

The cells were routinely grown in flasks with DMEM medium containing 4.5 g/l glucose, 10% foetal calf serum (FCS) and antibiotics at 37° C. and 6% CO$_2$. When the cell are confluent, they are trypsinised and seeded in 48-well plates as monolayers for 24 h.

For (3), (4), (5) and (7), the Ru compounds are weighed, and dissolved in DMSO to 100 mM. They are diluted in excess medium and diluted to 100 µM, such that the DMSO concentration did not exceed 0.12%. The 100 µM Ru complex solution was then serially diluted to make up 50 µM 25 µM 12.5 µM, 6.3 µM, 3.1 µM 1.6 µM solutions. The media is removed from the cell plates are the drug solutions applied in triplicate. A set of control cells, with media containing 1.0% DMSO, was left on each plate. The cells were exposed to the drugs for 72 hours.

For RAPTA-C, (8) and (9), the Ru compounds are weighed, and dissolved directly in medium to 1600 µM, then serially diluted to make up 800 µM, 400 µM, 200 µM, 100 µM, 50 µM, 25 µM solutions. The media is removed from the cell plates are the drug solutions applied in triplicate. A set of control cells, with media containing 1.0% DMSO, was left on each plate. The cells were exposed to the drugs for 72 hours.

Cell viability was determined using the standard MTT assay protocol, which allows the quantification of the mitochondrial activity in metabolically active cells. MTT (final concentration 0.2 mg/ml) was added to the cells for 2 h, then the culture medium was aspirated and the violet formazan precipitate dissolved in 0.1 N HCl in 2-propanol. The optical density, which is directly proportional to number of surviving cells, was quantified at 540 nm using a multiwell plate reader and the fraction of surviving cells was calculated from the absorbance of untreated control cells.

Figure 7:
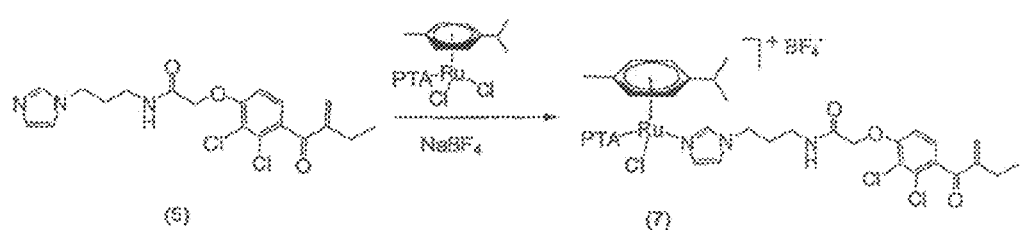
FIG. 7 illustrates the process for preparing (7), an example of an charged organometallic compound of the invention, present as its tetrafluoroborate salt.
Figure 8:
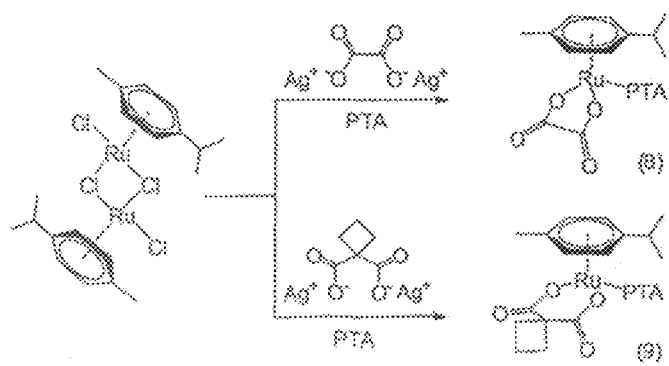
FIG. 8 illustrates the process for preparing (8) and (9), organometallic compounds that are used as controls for evaluating the activity of organometallic compounds of the invention.

Results:

Using the above protocol, the compounds were tested against human T47D and MCF-7 breast carcinoma, A549 lung carcinoma and HT-29 colon carcinoma cell lines (see FIG. 7).

TABLE 2

Comparison of activity between RAPTA-C and Ru-ethacrynic acid derivatives

| Complexes | IC$_{50}$(µM) | | | |
|---|---|---|---|---|
| | HT29 | A549 | T47D | MCF7 |
| ($\eta^6$-cymene)Ru(PTA)Cl$_2$ | 436 | 1029 | 1063 | >1600 |
| Ethacrynic acid | 73.5 | 50.7 | 7.73 | 66.0 |
| (Ethacrynic-$\eta^6$: phenylmethylamide)Ru(PTA)Cl$_2$ (3) | 50.7 | 32.3 | 2.91 | 19.9 |
| (Ethacrynic-$\eta^6$: phenylethanoate)Ru(PTA)Cl$_2$ (4) | 105.5 | 66.7 | 6.28 | 104.7 |
| ($\eta^6$-cymene)RuCl$_2$(ethacrynic-propylamide-imidazole) (6) | 39.1 | 34.0 | 4.80 | 10.7 |
| [($\eta^6$-cymene)RuCl(PTA)(ethacrynic-propylamide-imidazole)]BF$_4^-$ (7) | 64.2 | 65.1 | 5.97 | 19.9 |

TABLE 3

Comparison of activity between RAPTA-C and RAPTA-C carboxylate derivatives

| Complex | IC$_{50}$(µM) | | | |
|---|---|---|---|---|
| | HT29 | A549 | T47D | MCF7 |
| ($\eta^6$-cymene)Ru(PTA)Cl$_2$ | 436 | 1029 | 1063 | >1600 |
| ($\eta^6$-cymene)Ru(PTA)(C$_2$O$_4$) (8) | 267 | 1130 | 1174 | >1600 |
| ($\eta^6$-cymene)Ru(PTA)(C$_6$H$_6$O$_4$) (9) | 265 | 1567 | 1088 | >1600 |

Example 8

IC$_{50}$ Values of Compounds Tested on Tumor Cell Lines

Tumor cell lines derived from human and mouse tumours listed below were stabilised for in vitro propagation.

TABLE 4

Tumor cell lines for in vitro study.

| Identification | Tumor histotype |
|---|---|
| HT-29 [1] | Human colorectal carcinoma |
| MIA-PaCa-2 [2] | Human pancreatic cancer |
| H460M [3] | Human lung carcinoma/metastatic |

TABLE 4-continued

Tumor cell lines for in vitro study.

| Identification | Tumor histotype |
|---|---|
| A2780 | Human ovarian carcinoma |
| A2780/CDDP [4] | Human ovarian carcinoma resistant to Cistplatin |
| TLX5 [5] | Mouse lymphona |

[1] Obtained from CRO, Aviano, Italy (Dr. P. Spessotto);
[2] Obtained from Istituto Nazionale per lo Studio e la Cura dei Tumori, Milan (kindly supplied by Dr. D. Coradini);
[3] as [2], but kindly supplied by Dr. G. Pratesi;
[4] A2780cis is the variant of the parental A2780 resistant to Cisplatin (ECACC No. 93112517);
[5] Originally obtained from Chester Beatty Institute, London, UK.

$IC_{50}$ values are determined as follows: Tumour cells are incubated in the appropriate complete medium at 37° C. and under controlled atmosphere (5% CO2). Test compounds are tested at doses in the range of 100 nM and 100 µM. Cytotoxicity is determined by the MTT test, by measuring cell viability as the cell metabolic capacity to transform the tetrazolium salt of MTT in the blue formazan, by mitochondrial dehydrogenases; the blue colour is read at 570 nm with a spectrophotometer (Alley M C, Scudiero D A, Monks A, Hursey A L, Czerwinski M J, Fine D L, Abbott B J, Mayo J G, Shoemaker R H, Boyd M R. *Feasibility of drug screening with panels of human tumor cell lines using a microculture tetrazolium assay. Cancer Res* 48: 598-601, 1988. Mosmann T. *Rapid colorimetric assay for cellular growth and survival: application to proliferation and cytotoxicity assays. J Immunol Methods* 65: 55-63, 1983). Briefly, on day 0, in 96-well plates, 2-4000 cells/well/100 µl complete medium are plated. On day 1, test compounds are added at the test concentrations of $10^{-7}$ M; $3*10^{-7}$ M; $10^{-6}$ M; $3*10^{-6}$ M; $10^{-5}$ M; $3*10^{-5}$ M; $10^{-4}$ M. Each concentration is studied in triplicate. Cell viability, as determined by the MTT test is done on Day 4, after 3 days treatment. Each well is added with 10 µl/100 µl MTT (prepared previously by dissolving 5 mg/ml MTT in PBS, sterilized with filters at a cut-off of 0.22 mm and stored at 4° C.). Plates are put in an incubator at 37° C. for 4 hrs, then medium is eliminated and each well is added with 200 µl DMSO (Sigma Chemical Co., USA). Plates are read with a spectrophotometer (Spectra count Packard Bell, Meriden, Conn., USA) at 570 nm wave length. $IC_{50}$ is calculated with the GraphPad Prism4.

The table below shows the $IC_{50}$ values for the tested compounds. The reported values are the most representative of two separate experiments. Test concentrations have been done by serial dilutions of each compound starting form a mother solution of 10-2 M prepared by dissolving Compound 3, Compound 4, Ethacrynic acid and cisplatin in dimethyl-sulfoxide, and RAPTA-T (the moiety of the test compounds without the Ethacrynic acid moiety) in sterile apirogen water.

TABLE 5

| | $IC_{50}$ values (µM) | | | | | |
|---|---|---|---|---|---|---|
| | A2780 | A2780/CDDP | H460M | HT-29 | MIA PaCa-2 | TLX5 |
| Comp. 3 | 7.1 ÷ 9.5 | 4.6 ÷ 5.3 | 2.5 ÷ 3.8 | 2.3 ÷ 3.8 | 14.7 ÷ 20.1 | 0.8 ÷ 3.0 |
| Comp. 4 | ~30 | 36.7 ÷ 38.7 | 29.1 ÷ 31.5 | 30.0 ÷ 32.6 | 81.5 ÷ 92.7 | 3.6 ÷ 4.3 |
| Ethacrynic acid | 91.1 ÷ 94.8 | 84.3 ÷ 97.6 | 58.1 ÷ 63.3 | 35.2 ÷ 44.0 | >100 | 1.3 ÷ 1.8 |
| Cisplatin | 10.5 ÷ 11.8 | >100 | 1.3 ÷ 3.0 | 4.9 ÷ 32.6 | 10.6 ÷ 12.9 | 0.02 ÷ 0.2 |
| RAPTA-T | >100 | >100 | >100 | >100 | >100 | 64.1 ÷ 92.9 |

It can be seen from the table above that both compounds 3 and 4 of the present invention are active, in particular also against the Cisaplatin-resistant cell line A2780/CDDP.

Example 9

In-vivo Study

Tumour cells (TLX5, see above in Example 8) were derived from mouse tumours and stabilised for in vivo propagation. For the animal study, TLX5 lymphona cells were injected in the peritoneal cavity of CBA brown-grey inbred mice (Harlan-Nossan, San Giovanni al Natisone, Udine, Italy) at day 0. Test compounds were applied at day 3 at various doses, also by the intraperitoneal route, with each drug (test compound or reference drug) diluted in appropriate physiological solution and injected in a volume of 0.1 ml/10 g body weight.

Results from the in vivo study are shown in the table below.

TABLE 6

Survival time in an in vivo TXL5 lymphoma model

| | Mean survival time (days ± SD) | % increase vs Controls |
|---|---|---|
| Controls | 10.0 ± 0.82 | — |
| Compound 3 at 200 mg/kg | 12.2 ± 1.79** | 22 |
| Cisplatin 8 mg/kg | 11.8 ± 1.79* | 18 |

As can be seen from the table above, control mice die 10 after tumor inplant. The treatment with compound 3 raises the mean survival time to 12.2 days, corresponding to +22% versus control, a result statistically significant (** p=0.0089, Logrank test). Cisplatin, known to have severe side effects, was also effective at the dose indicated, although to a lesser extent (* p=0.0182).

While these results indicate that Compound 3 of the present invention is active in vivo, it is to be noted that the compound was administered as a suspension of the compound in carboxymethylcellulose. This fact has most probably reduced the bioavalability of the compound 3.

The invention claimed is:

1. An organometallic compound of formula (XIV),

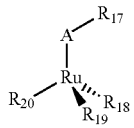

(XIV)

in which,

A is a monocyclic arene selected from the group of benzene, methylbenzene, cymene;

$R_{18}$, $R_{19}$, $R_{20}$, are ligands of the central ruthenium atom which are, independently of each other, selected from the group of halogens consisting of $F^-$, $Cl^-$, $Br^-$ and $I^-$, from the group consisting of N-, P- and O-donor ligands or from a bioactive organic compound;

$R_{17}$ is an optional residue selected from alkyl, alkenyl, alkynyl, aryl, or from a bioactive organic compound;

whereby at least one of $R_{17}$, $R_{18}$, $R_{19}$, and $R_{20}$ is a bioactive organic compound or whereby a bioactive organic compound is covalently linked to any of $R_{17}$, $R_{18}$, $R_{19}$, or $R_{20}$ via a covalent bond selected from the group consisting of a carbon-carbon alkyl bond, alkenyl bond and alkynyl bond, or selected from the group of carbon-heteronuclear bonds consisting of amide bond (—CONH—), ester bond (—CO$_2$—), ether bond (—CH$_2$O—), thioether (—CH$_2$S—), amine bond (—CH$_2$N—), imine bond (—CH═N—), and phosphorous bond (—CH$_2$P—), and wherein the bioactive organic compound is selected from:

an inhibitor of Glutathione S-transferase selected from ethacrynic acid, peptidomimetics of gluthatione, p-chlorophenoxyisobutyrate, Gossypol, indomethacin, non-steroidal anti-inflammatory compounds of ibuprofen and of ketoprofen, misonidazole, Piriprost, and Sulfasalazine;

an inhibitor of γ-Glutamyl Cysteine Synthetase selected from buthinone sulfoxime, methinone sulfoxime, S-sulfocysteine, S-sulfohomocysteine, and cystamine;

an inhibitor of the multidrug resistance protein selected from the group of quinidine, vinblastine, terfernadine, tamoxifen, verapamil, cyclosporin, amitriptyline, and progesterone; or an inhibitor of a cell signaling pathway selected from the group of pleurotin, azelaic acid, bischloroethylnitrosourea, and palmarumycin; and wherein said N-donor ligand is an imidazole of formula (IV) or of formula (V) which is covalently linked to the bioactive organic compound

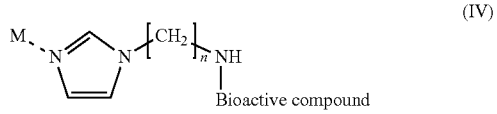

(IV)

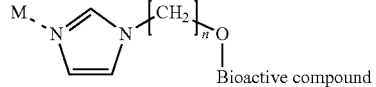

(V)

and wherein the "bioactive compound" moiety of formula (IV) and formula (V) represents a bioactive organic compound as described above and wherein the bioactive organic compound is linked to the —NH— of formula (IV) or the —O— of formula (V) via a carboxy group;

n is 1-10, and M is the transition metal Ru of the organometallic compound of formula (XIV);

said P-donor ligand is selected from the group consisting of PTA, MePTA and DAPTA, wherein PTA is 1,3,5-triaza-7-phosphadamantane, MePTA is 3-methyl-1,3,7-triaza-5-phosphabicyclo[3.3.1]nonane and DAPTA is 3,7-diacetyl-1,3,7-triaza-5-phosphabicyclo[3.3.1]nonane; and said O-donor ligand is selected from the group consisting of carbonate $CO^{3-}$; carboxylate ligands $R^CCO^{2-}$, oxalate $C_2O_4^{2-}$; nitrate $NO_3^-$; sulfate $SO4^{2-}$ and sulphonate $R^{S1}O_3-$, wherein $R^C$ and $R^{S1}$ are independently selected from alkyl, alkenyl, alkynyl, and aryl.

2. The organometallic compound according to claim 1, wherein:

$R_{20}$ and $R_{19}$ are independently selected from the group of halogens consisting of $F^-$, $Cl^-$, $Br^-$ and $I^-$; or from the group consisting of said P- and said O-donor ligands;

$R_{17}$ is present and -A-$R^{17}$ of formula (XIV) is represented by formula (XI) or formula (XII) below:

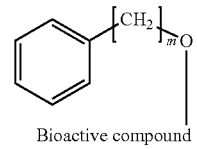

(XI)

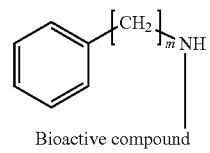

(XII)

wherein m is 1-10, the monocyclic arene A of formula (XIV) is the structure

and the "bioactive compound" of formula (XI) and formula (XII) represents the bioactive organic compound and wherein the bioactive organic compound is linked to the —O— of formula (XI) or the —NH— of formula (XII) via a carboxy group; and $R_{18}$ is selected from the group of halogens consisting of $F^-$, $Cl^-$, $Br^-$ and $I^-$ or from the group consisting of said P- and said O-donor ligands.

3. The organometallic compound according to claim 2, wherein $R_{20}$ and $R_{19}$ are independently selected from the group of $F^-$, $Cl^-$, $Br^-$ and $I^-$; and
$R_{18}$ is selected from the group consisting of said P-donor ligands.

4. The organometallic compound according to claim 2, wherein $R_{20}$ and $R_{19}$ are $Cl^-$; and
$R_{18}$ is selected from the group consisting of said P-donor ligands.

5. The organometallic compound according to claim 2, wherein $R_{20}$ and $R_{19}$ are independently selected from the group of halogens consisting of $F^-$, $Cl^-$, $Br^-$ and $I^-$; and
$R_{18}$ is the P-donor ligand PTA.

6. The organometallic compound according to claim 1, wherein A is benzene or cymene.

7. The organometallic compound according to claim 1, wherein said bioactive organic compound is ethacrynic acid.

8. The organometallic compound according to claim 1, wherein:
halogen is $Cl^-$; said P-donor ligand is PTA; said O-donor ligand is selected from carboxylate ligands $R^C CO^{2-}$ or oxalate $C_2O_4^{2-}$, wherein $R^C$ is selected from alkyl, alkenyl, alkynyl, and aryl; and said bioactive organic compound is ethacrynic acid.

9. The organometallic compound according to claim 1, wherein $R_{20}$ and $R_{19}$ are independently selected from the group of halogens consisting of $F^-$, $Cl^-$, $Br^-$ and $I^-$ or from the group consisting of said P-donor ligands;
$R_{18}$ is selected from said N-donor ligands of formula (IV) and of formula (V); and
$R_{17}$ is absent.

10. The organometallic compound of claim 1, which is selected from the group consisting of (Ethacrynic-$\eta^6$:phenyl-methylamide)Ru(PTA)Cl$_2$, (Ethacrynic -$\eta^6$:phenylethanoate)Ru(PTA)Cl$_2$, ($\eta^6$-cymene)RuCl$_2$(ethacrynic-propylamide-imidazole), and [($\eta^6$-cymene)RuCl(PTA)(ethacrynic-propylamide-imidazole)]BF$_4^-$, wherein PTA is 1,3,5-triaza-7-phosphadamantane.

11. A composition for treatment of cancer and/or metastasis comprising an anti-cancer drug and the organometallic compound of claim 10.

12. The organometallic compound according to claim 1, wherein:
$R_{20}$ and $R_{19}$ are independently selected from the group of halogens consisting of $F^-$, $Cl^-$, $Br^-$ and $I^-$; or from the group consisting of said P—and said O-donor ligands;
$R_{18}$ is selected from said N-donor ligands of formula (IV) and of formula (V); and
$R_{17}$ is present and is selected from alkyl, alkenyl, alkynyl, and aryl.

13. The organometallic compound according to claim 1, wherein:
$R_{20}$ and $R_{19}$ are independently selected from the group of halogens consisting of $F^-$, $Cl^-$, $Br^-$ and $I^-$; or from the group consisting of said P- and said O-donor ligands;
$R_{18}$ is selected from said N-donor ligands of formula (IV) and of formula (V); and
$R_{17}$ is absent.

14. The organometallic compound according to claim 1, wherein $R_{20}$ and $R_{19}$ are independently selected from the group of halogens consisting of $F^-$, $Cl^-$, $Br^-$ and $I^-$ or from the group consisting of said P-donor ligands;
$R_{18}$ is selected from said N-donor ligands of formula (IV) and of formula (V); and
$R_{17}$ is present and is selected from alkyl, alkenyl, alkynyl, and aryl.

15. The organometallic compound according to claim 1, wherein $R_{20}$ and $R_{19}$ are selected from the group of said O-donor ligands consisting of carboxylate ligands $R^C CO^{2-}$ and oxalate $C_2O_4^{2-}$, wherein $R^C$ is selected from alkyl, alkenyl, alkynyl, and aryl;
$R_{18}$ is selected from said N-donor ligands of formula (IV) and of formula (V); and
$R_{17}$ is selected from alkyl, alkenyl, alkynyl, and aryl.

16. The organometallic compound according to claim 1, wherein $R_{19}$ is selected from the group of halogens consisting of $F^-$, $Cl^-$, $Br^-$ and $I^-$ and $R_{20}$ is selected or from the group consisting of said P-donor ligands;
$R_{18}$ is selected from said N-donor ligands of formula (IV) and of formula (V); and
$R_{17}$ is selected from alkyl, alkenyl, alkynyl, and aryl.

17. The organometallic compound according to claim 1, wherein $R_{19}$ is selected from the group of halogens consisting of $F^-$, $Cl^-$, $Br^-$ and $I^-$ and $R_{20}$ is selected from the group consisting of said P-donor ligands;
$R_{18}$ is selected from said N-donor ligands of formula (IV) and of formula (V); and
$R_{17}$ is absent.

18. The organometallic compound according to claim 1, wherein:
A is cymene;
$R_{20}$ and $R_{19}$ are independently selected from the group of halogens consisting of $F^-$, $Cl^-$, $Br^-$ and $I^-$; or from the group consisting of said P- and said O-donor ligands;
$R_{18}$ is selected from said N-donor ligands of formula (IV) and of formula (V); and
$R_{17}$ is absent.

19. A composition for treatment of cancer and/or metastasis comprising an anti-cancer drug and the organometallic compound of claim 1.

* * * * *

UNITED STATES PATENT AND TRADEMARK OFFICE
CERTIFICATE OF CORRECTION

PATENT NO. : 9,018,199 B2
APPLICATION NO. : 12/227210
DATED : April 28, 2015
INVENTOR(S) : Paul Joseph Dyson and Wee Han Ang Page 1 of 1

It is certified that error appears in the above-identified patent and that said Letters Patent is hereby corrected as shown below:

In the Specification

Column 7, line 51 "$R_5$" should read --$R_8$--.

Column 8, Formula (X) should read

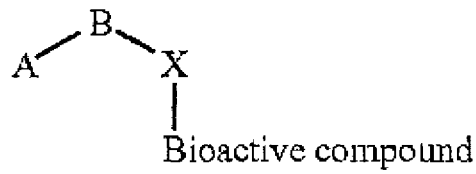

(X)

Column 16, line 62 "(imidazolium-ethacrynic aide)" should read --(imidazolium-ethacrynic amide)--.

Column 21, line 23, "Hursey A L" should read --Hursey ML--.

In the Claims

Claim 3 at column 25, line 3 "$^{, CL\text{-}}$" should read --, CL$^-$--.

Claim 3 at column 25, line 3 "$^{; and}$" should read --; and--.

Claim 9 at column 25, line 27 "$^{, CL\text{-}}$" should read --, Cl$^-$--.

Claim 14 at column 26, line 11 "$^{, CL\text{-}}$" should read --, Cl$^-$--.

Claim 16 at column 26, line 26 "$^{and}R_{20}$" should read --and $R_{20}$--.

Signed and Sealed this
Third Day of November, 2015

Michelle K. Lee
*Director of the United States Patent and Trademark Office*